United States Patent
Moon et al.

(10) Patent No.: US 7,135,338 B2
(45) Date of Patent: Nov. 14, 2006

(54) METHODS FOR OVEREXPRESSION OF HIGH MOLECULAR WEIGHT FORM OF MANNOSE BINDING LECTIN (MBL) AND A SPECIFIC FORMULATION FOR ACTIVE TREATMENT FOR SYSTEMIC INFECTION WITH MICROORGANISM

(75) Inventors: Hong Mo Moon, Englewood Cliffs, NJ (US); Jung-Sun Yum, Kyonggi-Do (KR); Byung Cheol Ahn, Kyonggi-Do (KR)

(73) Assignee: Dobeel Corporation, Kyonggi-Do (KR)

( * ) Notice: Subject to any disclaimer, the term of this patent is extended or adjusted under 35 U.S.C. 154(b) by 0 days.

(21) Appl. No.: 10/641,816

(22) Filed: Aug. 15, 2003

(65) Prior Publication Data

US 2004/0253601 A1 Dec. 16, 2004

(30) Foreign Application Priority Data

Jun. 11, 2003 (KR) .................. 10-2003-0037511
Jun. 24, 2003 (KR) .................. 10-2003-0041051

(51) Int. Cl.
*C12N 5/06* (2006.01)
*C12N 5/10* (2006.01)
*C12N 15/63* (2006.01)
*C12P 21/06* (2006.01)

(52) U.S. Cl. .................. 435/358; 435/69.1; 435/455

(58) Field of Classification Search ............ 435/320.1, 435/69.1, 455, 471, 325
See application file for complete search history.

(56) References Cited

U.S. PATENT DOCUMENTS 6,429,192 B1 * 8/2002 Laursen .................... 514/8

FOREIGN PATENT DOCUMENTS

WO  WO 00/70043  * 11/2000
WO  WO 02/14525 A2 * 2/2002

OTHER PUBLICATIONS

Vorup-Jensen et al. Recombinant expression of human mannan-binding lectin. International Immunopharmacology 1:677-687, 2001.*
Ohtani et al. High-level and effective production of human mannan-binding lectin (MBL) in Chinese hamster ovary (CHO) cells. Journal of Immunological Methods 222:135-144, 1999.*
Ma et al. Functional expression of human Mannan-binding proteins (MBPs) in human hepatoma cell lines infected with recombinant vaccinia virus. J. Biochem. 122:810-818, 1997.*

* cited by examiner

*Primary Examiner*—Celine Qian
*Assistant Examiner*—Quang Nguyen
(74) *Attorney, Agent, or Firm*—Gordon & Rees LLP

(57) ABSTRACT

This invention comprises of construction of a recombinant CHO cell line that produces functional mannose binding lectin (MBL) and of special uses of MBL. Specially, use of MBL for development of a therapeutic agent for patients having systemic infection with viruses, bacteria, or fungus is described. More specifically, MBL as a trigger for complement activation and MBL so formulated to activate complement system for the purpose of treating patients with microbial infection.

2 Claims, 7 Drawing Sheets

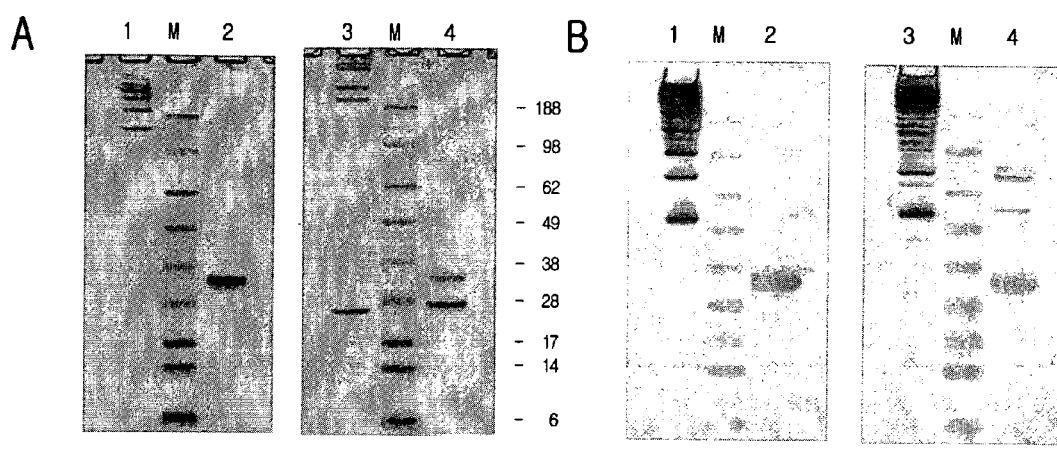

Fig.1. (A) SDS-PAGE Analysis of Purified MBL and (B) Western Blot Analysis Pattern.
Lane1. purified recombinant human MBL, non-reducing condition; lane2. purified recombinant human MBL, reducing condition; lane3. partially purified native MBL from human plasma, non-reducing condition; Lane4. partially purified native MBL from human plasma, reducing condition; lane M. molecular weight makers.
rhMBL shows similar pattern to the native MBL.

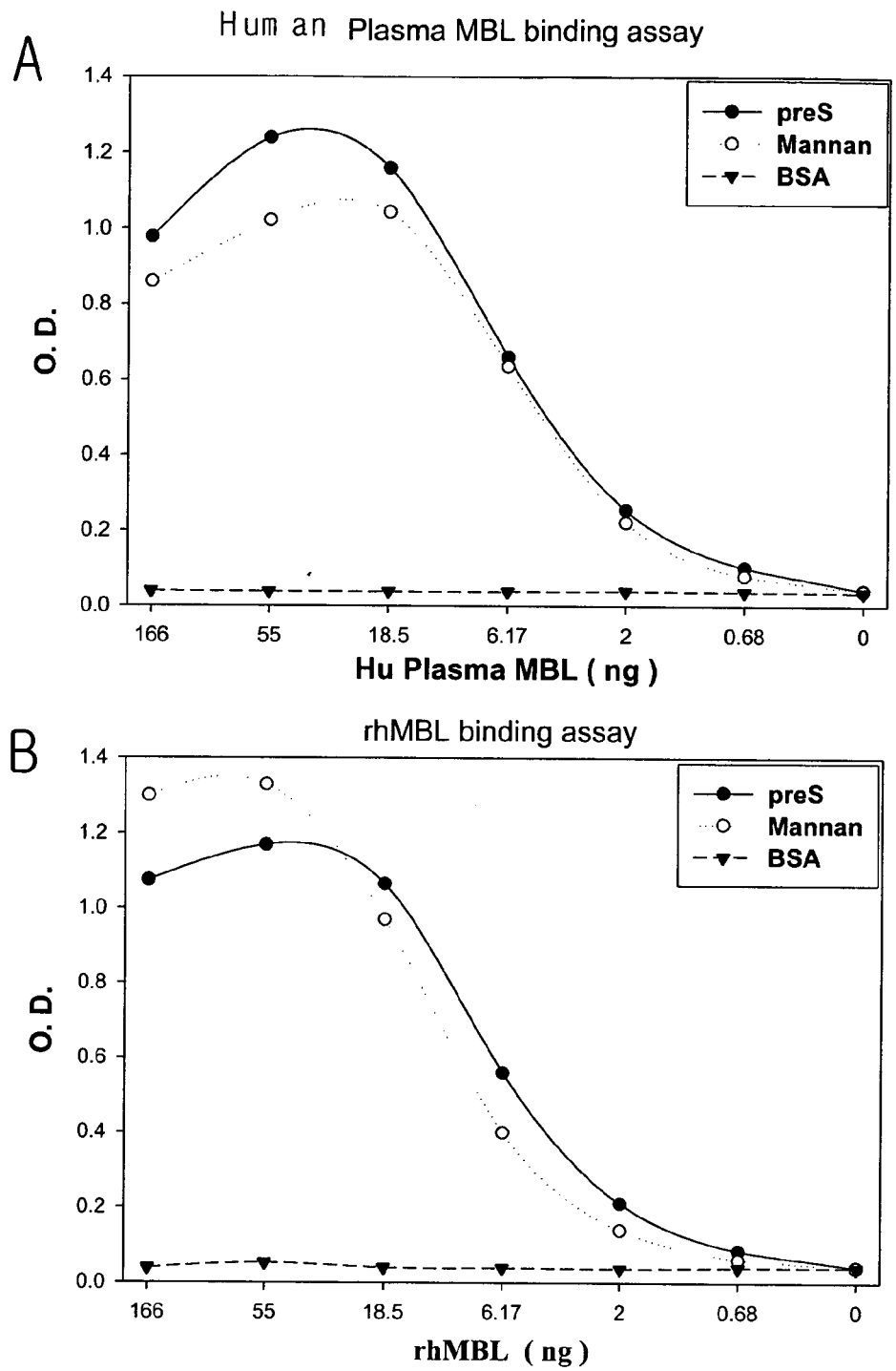
Fig. 2. MBL binding to glycosylated protein or mannan: A. human plasma MBL; B. rhMBL.
Both rhMBL and plasma MBL bind equally well to preS and mannan in a dose-dependent manner, but they don't bind to BSA.

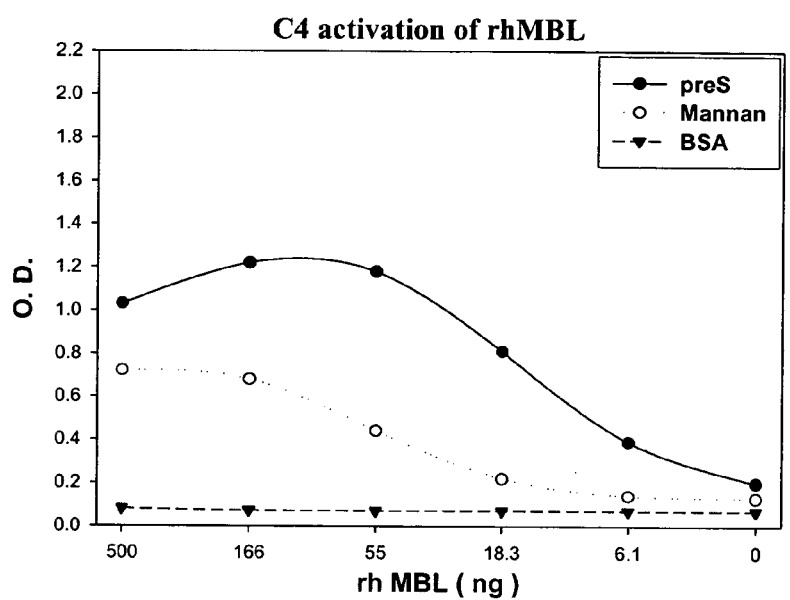
Fig. 3. Complement Activation (C4 cleavage) by rhMBL.
Complement activation was MBL dose dependent. As a source of MASPs, MBL free serum was used.

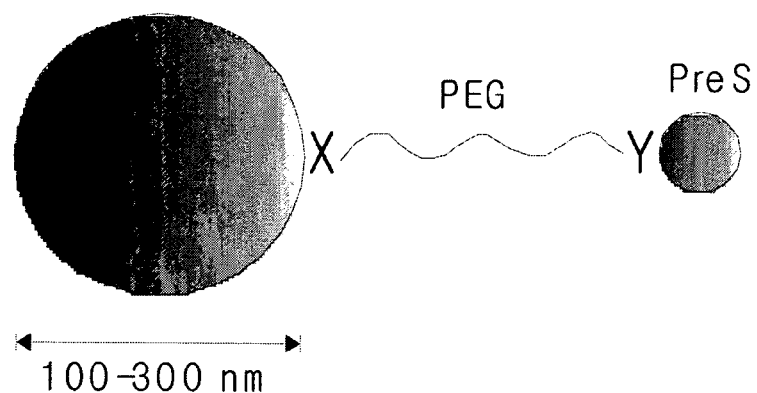
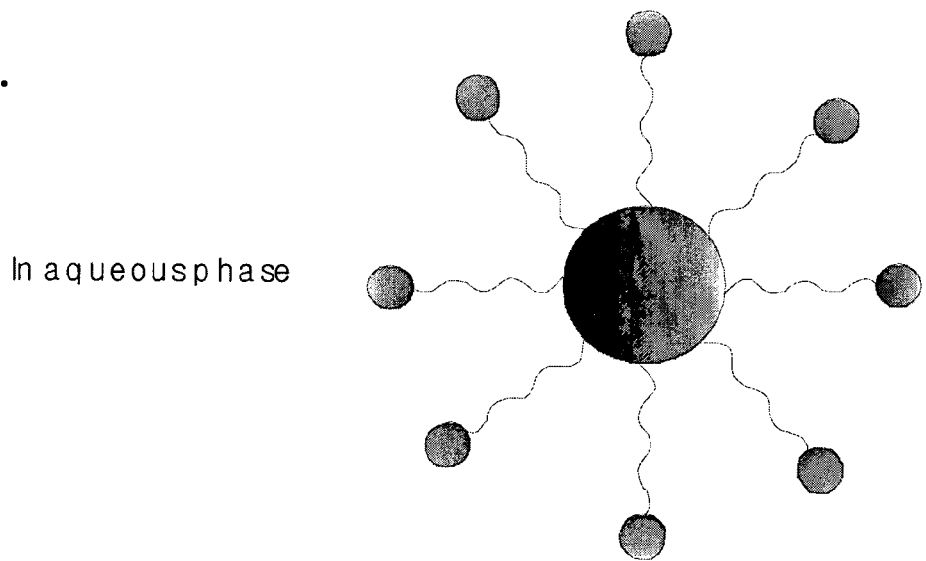
Fig. 4. pre S conjugated PLGA nano-particle (PLG-preS).
A.   PEG was used as a linker (See the example 5 for details).
B.   PLGA-pre S in aqueous phase

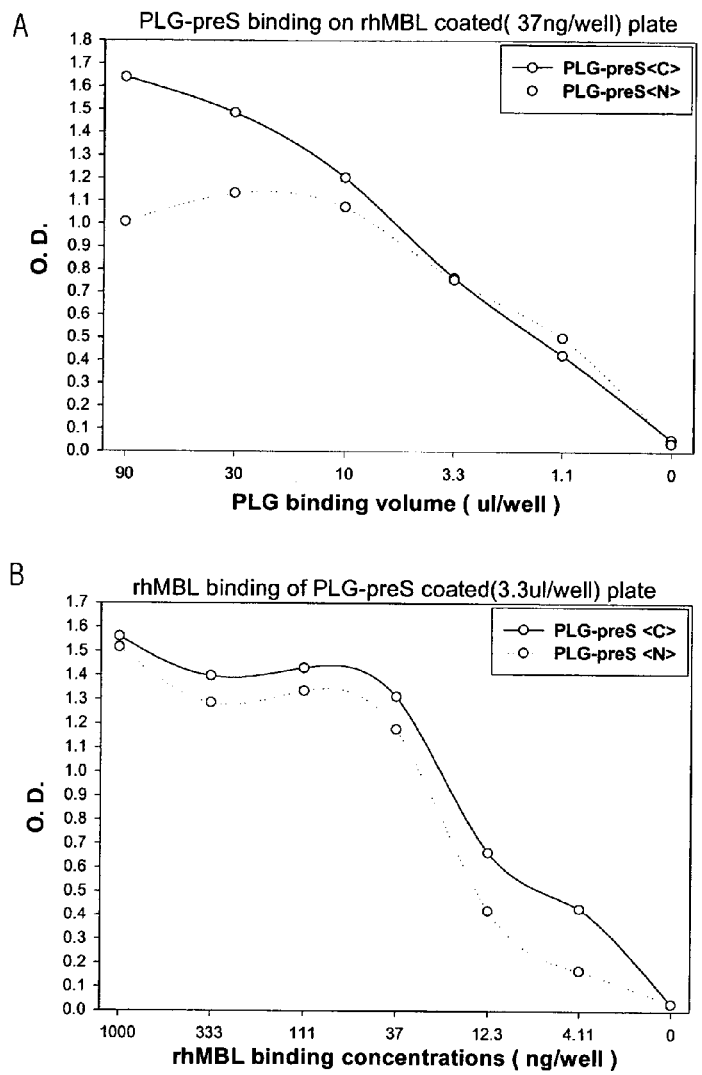
Fig. 5. MBL binding to PLG-preS.
(A) Using immunoplate coated with rhMBL, binding of PLG-preS to the plate was determined with various amount of PLG-preS. (B) PLG-preS was coated on to the plate and MBL binding was determined with increasing amount of rhMBL.

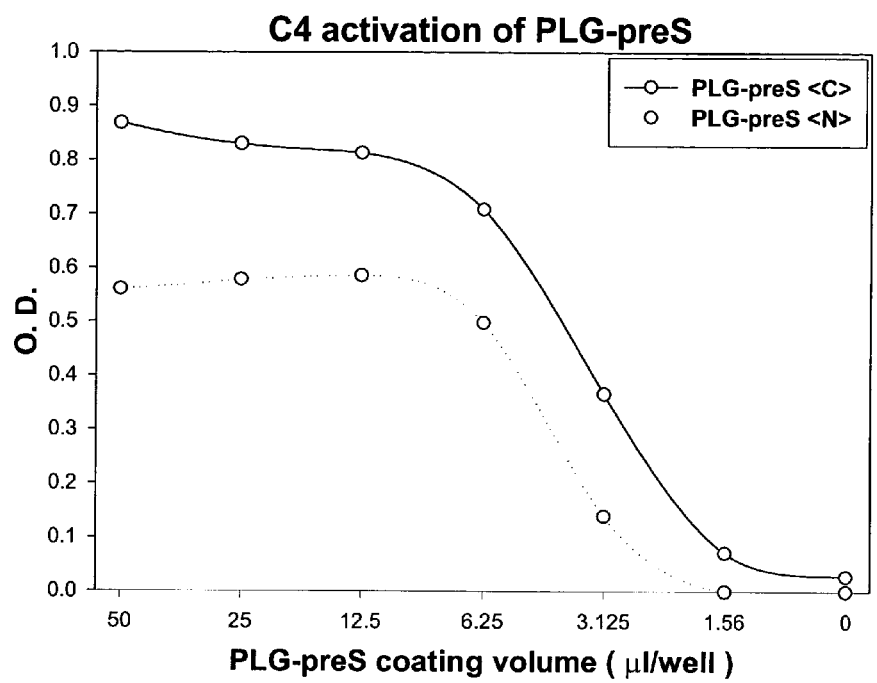
Fig. 6. Complement activation by PLG-preS and MBL.
rhMBL associated MASPs was activated to cleave C4 in the presence of increasing amount of PLG-preS. As a source of MASPs, MBL free human serum was used.

[Fig. 7] Neutralization of SARS-CoV by rhMBL.

SARS-CoV was infected to FRhK-4 cells in the presence of increasing amount of rhMBL. 2.5 μg/mL MBL in the culture media reduced the virus infection to less than 15% of the infection without MBL.

[Fig. 8] Microscopic picture of SARS-CoV infected cells in the presence or absence of MBL.

In the presence of 2.5 μg/mL MBL in the culture media (A), healthy cell are present, whereas dead cells and swollen cells are seen without MBL.

METHODS FOR OVEREXPRESSION OF HIGH MOLECULAR WEIGHT FORM OF MANNOSE BINDING LECTIN (MBL) AND A SPECIFIC FORMULATION FOR ACTIVE TREATMENT FOR SYSTEMIC INFECTION WITH MICROORGANISM

This application claims priority under 35 U.S.C. Section 119 to Korean Patent Applications 2003-0037511, filed Jun. 11, 2003; and 2003-0041051, filed Jun. 24, 2003.

FIELD OF THE INVENTION

The present invention is directed to recombinant human mannose-binding lectin (rhMBL), vectors and transformants for the production of recombinant MBL (rhMBL), use of rhMBL for prophylaxis and treatment of infection and/or immunedeficiency.

BACKGROUND OF THE INVENTION

MBL is a serum protein involved in innate immunity. The molecular weight is 32 KD, consisting of carboxy-terminal carbohydrate binding domain (CRD), collagen domain, and amino-terminal cysteine-rich region. The collagen domains of three MBL molecules form a triple helix resulting in a formation of a trimer, and then up to six units of the trimers form a giant molecule by inter molecular disulfide bonding using amino-terminal cysteines.

The MBL is associated with other proteins such as MBL associated serine proteases (MASP 1, MASP 2, or MASP 3) or MBL associated protein (Map19). Therefore, the overall molecular shape of MBL is similar to the first component of complement system (C1q). The function of activated MBL is also similar to C1q, but unlike C1q it activates complement system by cleaving C4 and C2. Activation of MBL requires binding of microorganisms with unique glycosylation pattern on their surface proteins. In this process the MBL associated serine protease is activated, and C4 and C2 are cleaved in a similar way that C1q associated serine proteases (C1r and C1s) triggers activation of complement system by cleaving C3. MBL binding to microorganism also prepares the microorganism for efficient phagocytosis, as if it is an opsonins.

Previously MBL gene has been expressed in various cell lines, including CHO cell (Katsuki Ohtani et al, J. of Inmunol. Methods 222, 135–144, 1999) or HLF hepatoma cell line or HEK 293 EBNA cell (T. Vorup-Jensen et al, International Immunopharmacology 1, 677–687, 2001).

High yield expression was possible in a CHO cell, but the MBL recovered was mainly monomers and dimers without significant amount of oligomers. Expression of MBL gene in transformed human cell lines produced significantly more oligomers, but the over all production yield was less than 1 ug/mL culture media.

It is well known that only high molecular weight form of MBL complex is capable of activating complement system. Activation of complement system is very important in defense against microbial infection. It not only prepares for invading microorganism for efficient phagocytosis and direct lysis, but also it helps efficient induction of adaptive immunity.

Serum level of MBL varies widely in different individuals, ranging from 50 ng/mL or lower to over 3 ug/mL serum mainly due to genetic variation. Genetic variation includes point mutations on exons and mutations on promoter regions. Generally individuals with low level of MBL are susceptible from microbial infection. Specially, those newborn children with low level of MBL are dangerously susceptible from infections. According to one survey (Y. Hakozaki et al, Liver, 22, 29–34, 2002), the mortality of patients going through hepatic failure due to Hepatitis B virus infection depended on the serum level of MBL. Patients with high level of MBL (3 ug/mL) did not die, whereas 80% of the patients with low MBL level died. Therefore those individuals with low MBL level might benefit from MBL supplement.

Therapeutic use of recombinant MBL requires not only high level expression of MBL for industrial quantity production but also high molecular oligomeric form of MBL.

SUMMARY OF THE INVENTION

We have successfully established recombinant CHO cell line that produces not only high amount of MBL (100 ug/mL culture media) but also significant amount of oligomeric form of MBL.

This invention provides a recombinant CHO cell line producing high molecular weight, oligomeric form of rhMBL for a large scale production to be used for industrial product development.

Further, this invention provides a new method for purification of rhMBL from the CHO cell culture media by using recombinant pre S protein as an affinity ligand. Further, this invention provides a convenient new method for determination of MBL activity by using recombinant pre S.

Further, this invention provides new formulations of MBL and methods of using them as triggers for complement activation. These formulations and methods provided are for treatment of acute patients with systemic infection by microorganisms.

BRIEF DESCRIPTION OF DRAWINGS

FIG. 1 Patterns of polyacrylamide gel electrophoresis (PAGE) and Western Blot analysis of purified MBL. This experiment was performed by conventional method under reducing and nonreducing condition. A. coomassie stained gel: Lane 1, nonreducing condition, rhMBL (1.2 µg); Lane 2, reducing condition, rhMBL (6 µg); Lane 3, nonreducing condition, plasma MBL (0.3 µg); Lane 4, reducing condition, plasma MBL (1.5 µg). B. Western Blot analysis: first antibody was polyclonal anti-human MBL (1:1,500 dilution), and the second antibody was anti-mouse IgG-HRP (1:5,000 dilution); Lane 1, rhMBL, nonreducing condition; Lane 2, rhMBL, reducing condition; Lane 3, plasma MBL, nonreducing condition; Lane 4, plasma MBL, reducing condition; Lane M, Molecular weight markers.

FIG. 2 Binding of MBL to glycosylated protein or mannan

Color was developed by using mouse monoclonal anti-human MBL (MBL8F6, 1:100 dilution, Dobeel) as first antibody and the second antibody was anti mouse IgG-HRP (1:1,500 dilution, KPL, USA). Color was developed with 150 µl/well of OPD (Sigma, USA), and color reaction was stopped with 50 µl/well of 3 M HCl. Color was measured by an automatic ELISA plate reader at 492 nm.FIG. 2a, human plasma MBL; FIG. 2b, rhMBL.

FIG. 3: Complement activation by rhMBL

C4 (500 ng/well) cleavage was detected with anti-C4 antibody-HRP (1:1,500 dilution, Biogenesis, UK). Color was developed with 150 1 OPD as for the FIG. 2.

FIG. 4: Illustration of pre S conjugation to PLGA nanoparticle and pre S coated PLGA particle. A. PEG was used as a linker (see the example 5 for details). PLGA-pre S in aqueous phase.

FIG. 5: rhMBL binding to PLGA-pre S

This experiment was carried out by the same way as for FIG. 2, except using plates coated with rhMBL or PLGA-pre S. When rhMBL was coated (FIG. 3A), binding of PLGA-pre S was detected with anti-pre S2 mAb (Aprogen, Korea). When PLGA-pre S was coated, MBL binding was detected with anti-MBL mAb (Dobeel, Korea).

FIG. 6: Complement activation by PLGA-pre S and MBL

Using PLGA-pre S (amine group conjugated, N or carboxyl group conjugated, C), complement activation assay was carried out as for FIG. 3.

FIG. 7: Neutralization of SARS-CoV by rhMBL 2.5 μg rhMBL/mL culture media prevented SARS corona Virus infection to FRhK-4 cells.

FIG. 8. Microscopic picture of FRhK-4 cells infected with SARS-CoV in the presence or absence of rhMBL. A. Healthy cells are seen in the presence of 2.5 μ/mL rhMBL, whereas cells are died or swollen in the absence of MBL.

DETAILED DESCRIPTION OF INVENTION

General Description and Definitions

The practice of the present invention will employ, unless otherwise indicated, conventional techniques within the skill of the art in (1) culturing animal cells, microorganisms, viruses, and bacteriophage; (2) biochemistry; (4) molecular biology; (5) microbiology; (6) genetics; (7) chemistry. Such techniques are explained fully in the literature. See, e.g. Culture of Animal Cells: A Manual of Basic Technique, 4th edition, 2000, R. Ian Freshney, Wiley Liss Publishing; Animal Cell Culture, eds. J. W. Pollard and John M. Walker; Plant tissue Culture: Theory and Practice, 1983, Elsevier Press; Maniatis et al., Molecular Cloning: A Laboratory Manual; Molecular Biology of The Cell, Bruce Alberts, et.al., 4th edition, 2002, Garland Science: Microbial Biotechnology, Fundamentals of Applied Microbiology, Alexander N. Glazer and Hiroshi Nikaido 1995, W.H. Freeman Co.; Pharmaceutical Biotechnology, eds. Daan J. A. Crommelin and Robert D. Sindelar, 1997, Harwood Academic Publishers; "Manual of Clinical Laboratory Immunology, eds. Noel R. Rose et al, 4th Edition, 1997, American Society for Microbiology).

The present invention involves the discovery of a new oligomeric form of rhMBL, which, in a therapeutic context, is intended to trigger the complement system for the treatment of systemic infection with virus, bacteria, or fungus. For this purpose recombinant MBL has been produced from a uniquely constructed recombinant CHO cell line and formulated to fulfill the therapeutic purpose. General techniques for recombinant protein production can be found in Mammalian Cell Biotechnology in Protein Production, eds. Hansjorg Hauser et al, 1997, Walter de Gruyter, Inc.

As described below in detail, in this invention the MBL gene-transformed cell line was a host cell transformed with pMSG-MBL. pMSG-MBL was constructed from pMGS (Korean patent, KCCM 10202, hereby incorporated by reference), having a DNA sequence consisting of nuclear matrix attachment region element of beta-globin gene sequence, SV40 poly A, and transcription termination sequence of gastrin gene and MBL cDNA. The MBL cDNA was prepared from a human liver cDNA library by PCR method. The host cell line is an animal cell, preferably Chinese Hamster Ovary (CHO) cell, human hepatocytes, and/or human embryonic kidney (HEK) cell. Other host animal cell lines are familiar to those of skill in the art, and find use in this invention In this invention as a non-limiting example, CHO cell was transformed with pMSG-MBL, and high expression clones were selected in the presence of increasing amount of methotrexate (MTX). The selected best clone was named CHO MBL/D1-3. The deposit of the MBL D1-3 (CHO cell line) was made on May 7, 2003, in the International Depositary Authority, Korean Collection for Type Cultures, located at Korea Research Institute of Bioscience and Biotechnology (KRIBB), #52, Oun-dong, Yusong-ku, Taejon 305-333, Republic of Korea. The deposited material was given accession number KCTC 10472BP. The deposit referred to herein will be maintained under the term of the Budapest Treaty on the International Recognition of the Deposit of Microorganisms for purposes of Patent Procedure. This deposit is provided merely as convenience to those of skill in the art and are not an admission that a deposit is required under 35 U.S.C. § 112. A license may be required to make, use, or sell the deposited materials, and no such license is hereby granted.

MBL produced from the CHO cell line showed high molecular weight multimeric forms, resembling natural MBL purified from human serum. This invention presents ways to produce high molecular weight, multimeric form of MBL. Further the CHO cell line produced a large quantity of functional MBL, making it possible to use the clone for industrial quantity of MBL production.

This invention presents a convenient method for purification of MBL from CHO MBL/D1-3 culture media, using recombinant pre S as an affinity ligand. For example, first pre S was immobilized on an appropriate column matrix, next packed onto a column, after this the column was equilibrated with an appropriate buffer. Finally, the culture media with MBL was loaded on to the column in the presence of calcium ion, eluting out MBL with a buffer containing EDTA or EGTA.

The column matrix can be any such matrix as sepharose.

In other work, we constructed a recombinant yeast cell line that produced pre S portion of Hepatitis B virus envelope protein (International Publication No. WO 02/094866, herein incorporated by reference.)

Purified recombinant pre S from this cell is highly glycosylated, and bound with MBL, and activated MBL for complement activation in the presence of MBL free serum as a source of MASPs. Consequently pre S was a very useful tool for convenient assay of MBL for functional activity. Further, the pre S can be used as a mean for purification of MBL from serum as well as from other sources such as recombinant MBL production.

Recombinant pre S was also used in a specific formulation of MBL for a direct trigger for complement activation. We prepared a PLGA [Poly(D,L lactic-co-glycolic acid)]-particle coated with pre S, which bound with MBL and activated complement in the presence of MBL free serum. According to our finding pre S in a solution made neither stable complex with MBL, nor did it activate MBL for complement activation.

Equilibration of the column was accomplished by using a buffer that afforded best binding of MBL to pre S. This buffer contained calcium ion in the range of 2 mM to 20 mM. The source of MBL to be purified can be human serum or any other material containing MBL such as culture media of CHO MBL/D1-3.

Elution of MBL from the column can be done with any solution containing EDTA or EGTA in the concentration range of 5 mM to 10 mM. If necessary this affinity column step can be repeated.

This purified MBL finds use in formulation of therapeutic agents. Methods for formulating MBL in a pharmaceutical delivery vehicle for administration to subjects for prophylaxis and treatment of infection are known (NatImmune A/S, Copenhagen, Denmark). This can be a formulation for individuals with no or low level serum MBL to strengthen defensive measure against microbial infection. Further MBL can be used as a formulation of active therapeutic agent for patients with systemic infection, by administering a much higher dose of MBL than normal serum level of MBL. This formulation can be MBL so formulated as a direct trigger for complement activation to treat patients with systemic infection of microorganism.

Pharmaceutical delivery vehicle formulations can include water, buffer solution, and/or stabilizers. Stabilizers include glycerol, glucose, sucrose, sorbitol, trehalose, maltose, albumin, and amino acids such as lysine or glycine. The amount of one or combination of these can be 3% to 30%. (See Goodman & Gilman's The Pharmacological Basis of Therapeutics, eds. Joel G. Hardman, Lee E. Limbird, Tenth Edition, 2001, McGraw Hill; Basic & Clinical Pharmacology, Bernard G. Katzung, Eighth Edition, 2001, McGraw Hill; Pharmaceutical Dosage Forms and Drug Delivery Systems, Howard C. Ansel, Loyd V. Allen, Jr., Nicholas G. Popovich, Seventh Edition, 1999, Lippincott, William & Wilkins; Harrison's Principles of Internal Medicine by Eugene Braunwald M.D. (Editor), Anthony S. Fauci M.D. (Editor), Dennis L. Kasper M.D. (Editor), Stephen L. Hauser M.D. (Editor), Dan L. Longo M.D. (Editor), J. Larry Jameson M.D. (Editor).

Formulation of MBL can include MBL associated proteins such as MASP 1, MASP 2, MASP 3, and/or Map19. These MBL associated proteins can be from natural sources or recombinant proteins.

Formulation of an effective amount of MBL can be in the form of oil suspension, solution, or solid. In case of solid it can be dissolved in a solution mentioned above before administration.

The route of administration of MBL can be ip, sc, im or iv injection or a combination.

This invention provides method of making MBL for use as a composition which comprises a pharmaceutical delivery vehicle which is administered to a human subject in need of it as a trigger for complement activation. An embodiment of the invention is a preparation which uses pre S coated on the surface of liposome or PLGA nano-particle.

The term nanoparticles includes particles which are hollow as well as filled particles. Methods for making nanoparticles (5 to 500 mn), either uniform in size or having a predefined complex size distribution, from biocompatible, biodegradable polymers are well known. The sphere-shaped particles can be formed from a variety of materials, including FDA-approved, biodegradable polymers such as poly (lactic-co-glycolic acid) and polyanhydrides. (incorporated by reference are U.S. patent application 20020054912, U.S. Pat. Nos. 5,948,483, 6,060,128, 5,344,676, International Publication #WO 02/13786 A2; Precise control of PLG microsphere size provides enhanced control of drug release rate," by C. Berkland, M. King, A. Cox, K. Kim, and D. W. Pack. Published in Journal of Controlled Release, 2002, 82(l):137–147; "Fabrication of PLG microspheres with precisely controlled and monodisperse size distributions," by C. Berkland, K. Kim and D. W. Pack. Published in the Journal of Controlled Release, 2001, 73(1):59–74; "Visual evidence of acidic environment within degrading PLGA microspheres," by K. Fu, D. W. Pack, A. M. Klibanov and R. Langer. Published in Pharmaceutical Research, 2000 17(1): 100–106; "PLGA microspheres containing plasmid DNA: preservation of supercoiled DNA via cryopreparation and carbohydrate stabilization," by S. Ando, D. Putnam, D. W. Pack and R. Langer. Published in Journal of Pharmaceutical Sciences, 1999, 88(1):126–130; Methods of preparing liposomes have been described (i.e., U.S. Pat. Nos. 5,653,996, 5,393,530 and 5,651,981, U.S. Pat. Nos. 5,595,756, 5,605, 703, 5,627,159, 5,652,225, 5,567,433, 4,235,871, 5,227,170, all incorporated by reference).

The size of nanoparticle ranges from 5 nm to 500 nm. The pre S can be replaced with any glycosylated protein or peptide or glycosyl moeity, e.g. mannose, that binds with MBL. Examples of glycosyl moieties include, but are not restricted to of mannose, N-acetyl glucosamine-rich oligosaccharides present on a wide range of bacteria, viruses, fungi, and parasites, glucans, and lipophosphoglycans and glycoinositol-phospholipids with mannose, glucose, fucose, or N-acetylglucosamine as N-terminal hexoses. Glycoproteins useful in the invention pre S glycosylated viral envelope protein, glycosylated bacterial protein, glycosylated fungal protein, i.e. and any artificially glycosylated protein which binds with MBL.

Free monomeric ligand such as pre S in solution does not activate MASPs. Whereas, pre S molecules immobilized onto solid surface make stable complex with MBL and activate MBL and complement system. Therefore our finding indicates that MBL complex activation is similar to C1 activation in that the activation of C1 complex requires engagement of multiple IgGs bound to cell surface antigens, but not with monomeric IgG molecule. Pre S conjugated onto the surface of PLGA nano-particle serves as an efficient activator of MBL complex.

This unique formulation of MBL as a trigger for complement activation can be broadly utilized for the treatment of patients with systemic infection by microorganism such as virus, bacteria, and/or fungus.

EXAMPLES

Example 1

Construction of MBL Producing CHO Cell Line 1.1 Construction of Expression Vector MBL cDNA was prepared by PCR method using a human liver cDNA library, and it was cloned into pEZ vector (RNA, Inc. Suwon, Korea), pEZ-MBL2-5. The nucleotide sequence was verified from sequence stored in Gene Bank (Gene Bank NM_000242). Using this pEZ-MBL2-5 DNA as a template, 750 bp MBL cDNA for MBL expression was prepared by PCR method with primer 1 and primer 2 (see the sequence listing). These primers include Kozak Sequence and restriction endonuclease sites for cloning. This cDNA was cloned into pMSG vector (PanGen Biotech Inc., Suwon, Korea; Korean Patent, KCCM 10202) to make pMSG-MBL. The MBL sequence was verified again with Gene Bank sequence.

```
Forward primer
ctagctagcc accatgtccc tgtttccatc actc      (34mer)
SEQ ID No. 1

Reverse primer
gaagatctca gatagggaac tcacagacg            (29mer)
SEQ ID No.2
```

1.2 Transfection of pMSG-MBL into Expression Host 1.2.1 Preparation of pMSG-MBL DNA After transfecting pMSG-MBL DNA into an appropriate E. coli, the transformant was cultured in 100 mL LB media containing 100 ug/mL ampicilin. From this culture pMSG-MBL was prepared by using QUIAPREP Plasmide Midi Kit (Quiagen, USA). The pMSG-MBL linear DNA was prepared by digesting with Sca I.

1.2.2. Preparation of Host Cell

CHO DG44 (dhfr-/dhfr-) was cultured in -MEM media containing 10% cFBS and the cell number was determined with a hematocytometer. Then the cell number was adjusted to $2 \times 10^5$/mL cell in alpha-MEM containing 10% cFBS and cultured 24 hr in a $CO_2$ incubator.

1.2.3 Transformation

A mixture containing 2 ug of pMSG-MBL DNA, 5.3 uL Dosper™, and 16 ng pDCH1P (Plasmid with DHFR gene, Venolia et al, 1987, Somat. Cell Mol. Genet. 13, 491–501) was incubated at room temperature for 45 min. Then the mixture was added to the host cell and incubated 6 hr. at 37 degree centigrade. After the incubation, media was removed and added 3 mL of fresh alpha-MEM containing cFBS. Then after 2–3 days when the transformed cells expanded enough, cells were harvested by trypsin treatment and $4 \times 10^5$ cell/well was grown in 2 mL of alpha-MEM without nucleosides containing 10% dialyzed FBS. Transformed cells were grown for about 10 days with media changes every 2–3 days.

1.3 Selection of MBL-producing Cell and Amplification of MBL Gene

Transduced MBL gene in the transformed cell was amplified by adding gradually increasing amount of MTX in the culture media. For this, cell number was adjusted to $4 \times 10^5$/well and cultured in the presence of 10 nM MTX until the cells reached confluent state. By a similar method, the concentration of MTX was increased to 1 uM. In each step the level of MBL expression was determined by Western blot analysis using anti-MBL. The level of MBL was increased as the concentration of MTX was increased, and a single clone was selected from the cell adapted to 1 uM MTX.

1.4 Selection of a Single Best Cell (Cloning)

For single cell cloning, 1 uM MTX adapted cells were distributed into a 96-well plate at 0.5 cell/well. This plate was cultured in alpha-MEM containing 10% dialyzed FBS and 1 uM MTX. About two weeks later when a single cell colony was formed, the cells were transferred to 24-well plate. When cells were expanded enough, cells were frozen after analyzing the expression level. One of the cell lines selected was CHO MBL/D1-3. FIG. 1 shows the pattern of Western blot analysis of MBL produced from the recombinant cell line after polyacrylamide gel electrophoresis under reducing and non-reducing conditions.

1.5 Estimation of MBL Expression Level

Using CHO MBL/D1-3 cell line, the level of MBL expression was estimated by comparing to a known amount of purified MBL from human serum. $5 \times 10^5$ cells were grown in a T25 flask with alpha-MEM without nucleosides containing 10% dialyzed FBS. When cell density reached 90% confluency, the media was replaced with 3 mL of the same media containing 5% dialyzed FBS. After 4 days the culture media was diluted 10 fold and the amount of MBL in the media was estimated to be 50 ug/$10^6$ cells/day.

Example 2

Purification of rhMBL 2.1 Preparation of Pre S-Sepharose Column

One gram of CNBr activated Sepharose 4B was suspended in 1 mM HCl solution and washed several times with the same solution. To this washed Sepharose 6.4 mg pre S (recombinant pre S from Yeast, patent; PCT/KR02/00820, hereby incorporated by reference) was mixed in a coupling buffer pH 8.3 containing 0.2 M NaHCO3 and 0.5 M NaCl to make final concentration of pre S to be 0.5–10 mg/mL. After incubating 2 hr at room temperature, blocking buffer pH 8.0 containing 0.1 M tris was added and left in the room temperature for 2 hr. Then pre S-Sepharose was washed with the blocking buffer and the amount of immobilized pre S was estimated by Western blot analysis.

2.2 Purification of MBL by Using Pre S-Sepharose Column

We have established a purification method by exploiting the nature of pre S binding to MBL. Pre S can be produced in large quantity from our recombinant yeast, which produces a large quantity of pre S in culture media. Pre S-Sepharose was packed into a column and equilibrated with MBL binding buffer containing 20 mM Tris pH 7.6, 150 mM NaCl, 10 mM CaCl2, and 0.05% Tween 20. The column was loaded with MBL in the CHO cell culture media or in serum and washed extensively with the loading buffer. Then the MBL was eluted from the column with elution buffer containing 20 mM Tris pH 7.6, 150 mM NaCl, 5 mM EDTA, and 0.05% Tween 20. In this manner, just one step yielded 99.9% pure MBL. See FIG. 1.

Example 3

Verification of Function of rhMBL

Biological activity of rhMBL was determined for two different functions; 1) specific binding of rhMBL to glycosylated protein in calcium dependent manner and 2) activation of complement (C4 cleavage) in the presence of glycosylated protein and MASPs.

3.1 Binding of rhMBL to Glycosylated Protein 3.1.1 Mannan Binding

So as to coat the plate with mannan, mannan solution in 50 mM carbonate-bicarbonate buffer was added to each well to make 1 ug/well on a Nunc Maxisorp Immunoplate and incubated overnight at 4 degrees centigrade. It was washed 4 times with washing buffer containing 20 mM Tris pH 7.6, 150 mM NaCl, 10 mM CaCl2, and 0.05% Tween-20 and treated with 0.2% BSA for 1 hr. After washing the plate 3 times with the washing buffer, 1 ug MBL/well was added in 100 uL of binding buffer containing 20 mM Tris pH 7.6, 1M NaCl, 10 mM CaCl2, 0.1% BSA, 0.05% Tween-20. After 2 hr incubation at room temperature, the plate was washed 6 times with the washing buffer and color was developed. First the plate was incubated with mouse monoclonal anti-human MBL (Dobeel, MBL8F6, 1:100 dilution) for 2 hr at room temperature. Next added was anti-mouse IgG-HRP (1:1500 dilution) and incubated 1 hr at room temperature. Finally color was developed by OPD (Sigma, USA). The color development was stopped by adding 3M HCl and the color was measured at 492 nm using an automatic ELISA plate reader. Mannan binding activity of rhMBL was compared with native MBL (FIG. 2). This experiment showed rhMBL was functionally similar to native MBL purified from human serum.

3.1.2 MBL Binding to Pre S

Employing the same method for MBL binding to mannan, MBL binding to pre S was carried out using 1 ug pre S (FIG. 2).

3.2 Complement Activation by rhMBL

3.2.1 Complement Activation with Mannan Coated Plate

Nunc Maxisorp Immunoplate wells were coated with 1 ug/well mannan as described in 3.1.1, and this plate was incubated 2 hr at room temperature with rhMBL or serum MBL. When rhMBL was used the MBL free serum was added as a source of MASPs. After 2 hr incubation, the plate was washed 6 times with the wash buffer and incubated 2 hr at room temperature with 500 ng/well C4. Then it was incubated 1 hr at room temperature with anti C4 antibody-HRP and color was developed by adding 150 uL OPD. After 20 min. the color reaction was stopped by adding 50 uL/well 3M HCl and OD was determined at 492 nm. This experiment showed that rhMBL had comparable activity in terms of C4 cleavage to serum MBL (Data not presented).

3.2.2 Complement Activation with Pre S Coated Plate

Similarly to 3.2.1 with pre S coated (1 ug/well) plate, MBL activity for complement activation was determined. The result showed that pre S was better than mannan in the activation of MBL associated serine protease (FIG. 4).

Example 4

Formulation of MBL as a Trigger for Complement Activation

4.1 Preparation of Pre S Coated Nanoparticle

4.1.1 Preparation of PLGA Nanoparticle

Poly(D,L-lactic-co-glycolic acid) [PLGA], molecular weight ranging from 1,000 to 100,000, was dissolved in an organic solvent such as methanol or methylene chloride. It was then dispersed on a solution of SDS or Tween and kept overnight with violent stirring. Nanoparticles were recovered from this.

4.1.1 Conjugation of PEG to the Nanoparticle

Poly(ethylene glycol) [PEG] with heterofunctional reaction groups (X-PEG-Y) was used. In an organic solvent or in water solution, the reaction group X was activated and then conjugated to reaction groups (—OH, —COOH) on the nanoparticle. Linkers (X—) used in this conjugation can be as shown in the following:

X:

$$-\overset{O}{\overset{\parallel}{C}}-\overset{}{\underset{H}{N}}- \quad -\overset{O}{\overset{\parallel}{C}}-O- \quad -S-S-$$

$$-O-\overset{O}{\overset{\parallel}{C}}-\underset{H}{N}-$$

4.1.3 Conjugation of Pre S to the Nanoparticle Conjugated to PEG

Conjugation of pre S can be accomplished through -amine on lysine and arginine or N-terminal amine. Alternatively C-terminal or -carboxylic acid can be used to make conjugation of pre S to PEG conjugated to the nanoparticle. In these free Y reaction group on PEG can be conjugated to the carboxylic acid or amine on the pre S. In this the linker (Y—) can be as following:

Y:

$$-\overset{O}{\overset{\parallel}{C}}-\underset{H}{N}- \quad -\overset{O}{\overset{\parallel}{C}}-O- \quad -S-S-$$

$$-O-\overset{O}{\overset{\parallel}{C}}-\underset{H}{N}-$$

Details of the procedures for protein conjugation to PLGA nano-particles are described in H. S. Yoo et al, J. Controlled Release, 82, 17–27, 2002 and S. H. Choi and T. G. Park, Intl. J. Pharmaceutics, 203, 193–202, 2000. The number of pre S conjugated to one PLGA particle is 100,000–300,000 pre S molecules/particle.

4.2 PLGA-pre S as a Functional Molecule for MBL Activation

Binding of rhMBL to PLGA-pre S and activation of complement by rhMBL-pre S-PLGA complex were carried out by the same methods employed in FIG. 2 and FIG. 3, respectively. The results are shown in FIG. 5 and FIG. 6. We found that MBL coated plate could not be used for complement activation presumably due to blocking the association of MASPs to immobilized MBL on to a solid surface. Therefore, we also carried out complement activation assay in a solution phase, including PLGA-pre S, MBL, MASPs, and C4. From this experiment we learned that monomeric pre S, unlike the PLGA-pre S, does not make stable complex with MBL, nor does it activate MBL-associated MASPs for complement activation (Data not presented).

Example 5

Neutralization of SARS-CoV by rhMBL

Infection of SARS-CoV on fetal rhesus kidney cell (FRhk-4) was carried out in the presence of various amount of rhMBL in the culture media. As shown in the histogram of FIG. 7 and microscopic pictures (FIG. 8), 2.5 ug/mL rhMBL blocked the virus infection, reducing the level of virus infection to less than 15% compare to the cells without MBL. The microscopic picture showed healthy cells in the presence of 2.5 ug rhMBL/mL culture media, whereas cells infected with the virus without MBL showed dead cells and swollen cells only. Considering that the normal MBL level in human serum is about 2.5 ug/ml, MBL was blocking the SARS-CoV in the presence of physiological concentration. Methods for growing SARS-CoV and detection of the virus by RT-PCR are described in Ksiazek T. G. et al, N. Engl. J. Med. 2003; 348, 20: 1953–66 and Peiris J. S. et al, Lancet 2003; 361, 9366: 1319–25.

What is claimed is:

1. A transformed host cell which comprises a DNA construct comprising a cloning vector which comprises:
   a) a sequence of a human mannose-binding lectin (MBL) coding region, said sequence being sufficient to express a recombinant MBL in said transformed host cell,
   b) an SV40 promoter DNA sequence operatively linked to said sequence of human MBL coding region,
   c) a sequence of nuclear matrix attachment region element of beta-globin gene sequence,
   d) an SV40 poly A, and
   e) a transcription termination sequence of a gastrin gene, said recombinant MBL exhibiting specific binding to pre S portion of Hepatitis B virus envelope protein and complement activation in the presence of MBL-binding glycosylated protein and serine proteases, wherein said transformed host cell is deposited to the International Depository Authority under the accession number KCTC 10472BP.

2. A method for producing recombinant MBL, said method comprising the steps of:
   (a) providing a transformed host cell which comprises a DNA construct comprising a cloning vector which comprises:
   a sequence of a human MBL coding region, said sequence being sufficient to express a recombinant MBL in said transformed host cell,
   an SV40 promoter DNA sequence operatively linked to said sequence of human MBL coding region,
   a sequence of nuclear matrix attachment region element of beta-globin gene sequence,
   an SV40 poly A, and
   a transcription termination sequence of a gastrin gene, said recombinant MBL exhibiting specific binding to pre S portion of Hepatitis B virus envelope protein and complement activation in the presence of MBL-binding glycosylated protein and serine proteases;
   (b) expressing in a cell culture system said sequence of human MBL coding region to produce recombinant MBL; and
   (c) purifying the recombinant MBL produced in step (b);
   wherein said transformed host cell is deposited to the International Depository Authority under the accession number KCTC 10472BP.

* * * * *

SEQUENCE LISTING

<160> NUMBER OF SEQ ID NOS: 2

<210> SEQ ID NO 1
<211> LENGTH: 34
<212> TYPE: DNA
<213> ORGANISM: Homo sapiens

<400> SEQUENCE: 1
ctagctagcc accatgtccc tgtttccatc actc    34

<210> SEQ ID NO 2
<211> LENGTH: 29
<212> TYPE: DNA
<213> ORGANISM: Homo sapiens

<400> SEQUENCE: 2
gaagatctca gatagggaac tcacagacg    29